United States Patent

Paez

[11] Patent Number: 5,121,753
[45] Date of Patent: Jun. 16, 1992

[54] KNEE ORTHOSIS MEASURING DEVICE

[75] Inventor: Juan B. Paez, Spring Arbor, Mich.

[73] Assignee: Camp International, Inc., Jackson, Mich.

[21] Appl. No.: 374,913

[22] Filed: Jul. 3, 1989

[51] Int. Cl.⁵ .................................. A61B 5/107
[52] U.S. Cl. ........................................ 128/774; 33/515
[58] Field of Search ............... 128/80 R, 782, 882, 128/774; 33/511, 512, 514.1, 514.2, 515

[56] References Cited

U.S. PATENT DOCUMENTS

| | | | |
|---|---|---|---|
| 4,033,329 | 7/1977 | Gregory et al. | 33/515 |
| 4,407,277 | 10/1983 | Ellison | 128/882 |
| 4,534,364 | 8/1985 | Lamoreux | 128/774 |
| 4,583,555 | 4/1986 | Malcolm et al. | 128/782 |

Primary Examiner—Lee S. Cohen
Assistant Examiner—K. M. Pfaffle
Attorney, Agent, or Firm—Beaman & Beaman

[57] ABSTRACT

Knee orthosis measurement apparatus for attaching to the leg including a linear column having measurement probes mounted thereon for engaging the leg. The probes are mounted upon a scale connected to the column whereby the position of the probes to the columns may be readily determined to compare the position of various locations of the leg to the column.

7 Claims, 1 Drawing Sheet

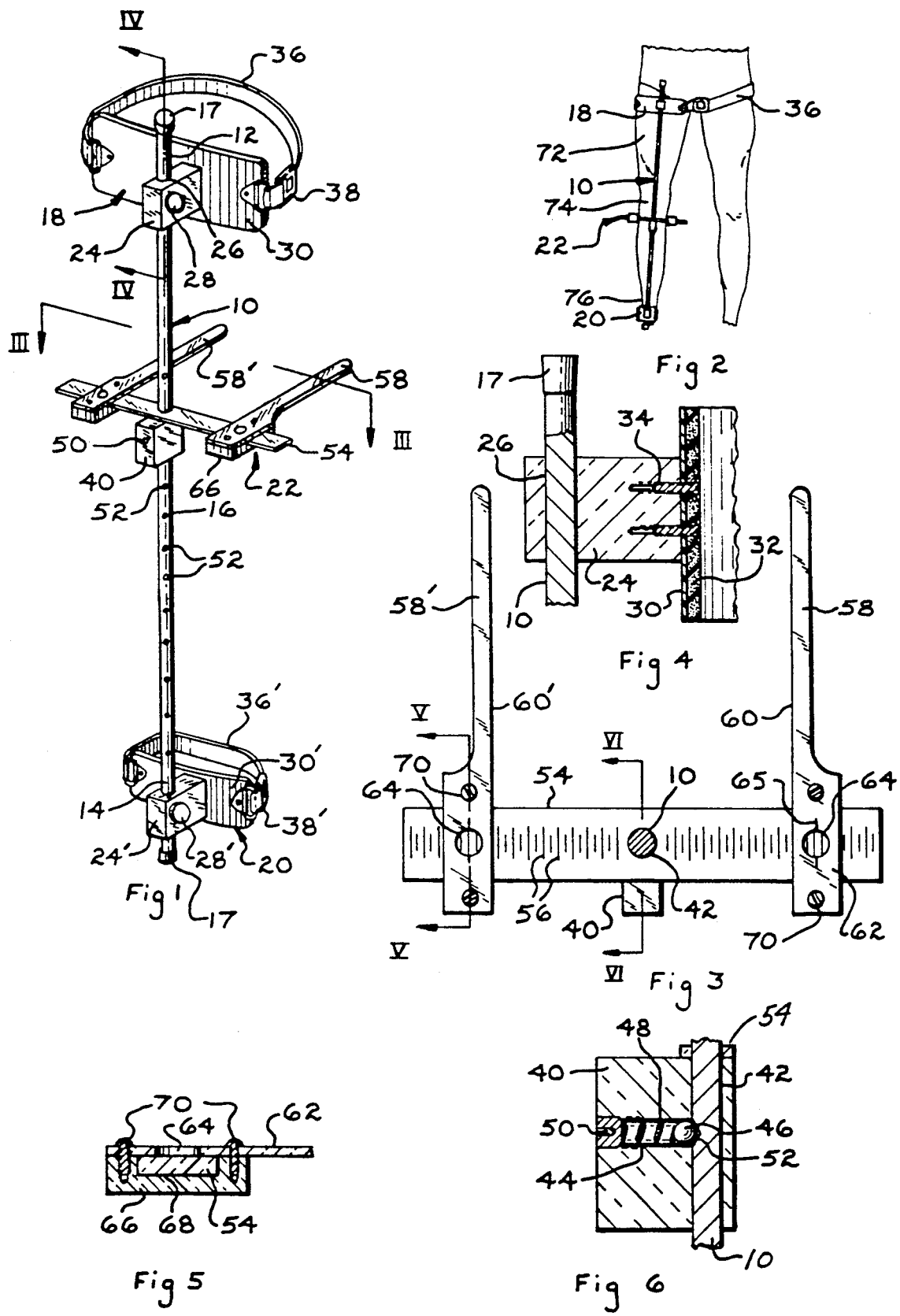

KNEE ORTHOSIS MEASURING DEVICE

BACKGROUND OF THE INVENTION

In treating the leg and knee, particularly when fitting orthosis apparatus to the leg and knee, it is desirable to be able to accurately measure the dimensions of the leg and knee and compare the limb measurements to a reference point. As each person's leg differs, to produce an orthosis of maximum efficiency and comfort accurate measurements are highly desirable, but heretofore, were not readily obtainable.

Various devices for measuring the position and movement of human limbs are known, typical devices being shown in U.S. Pat. Nos. 3,020,639; 4,436,099 and 4,742,832. However, known orthosis measuring devices are expensive, cumbersome to install and use, and require highly skilled technicians.

It is an object of the invention to provide an orthosis device for the leg and knee which is of economical manufacture, readily applied to the patient, is capable of providing accurate limb measurements relative to a reference, and may be utilized by technicians having limited skills.

A further object of the invention is to provide an orthosis measurement device for the leg and knee which is lightweight, easy to use, and permits a plurality of measurements to be quickly taken at various locations along the leg.

Yet another object of the invention is to provide a leg and knee orthosis measuring device wherein a plurality of portions of the leg may be quickly measured with respect to a reference column mounted in a predetermined manner to the leg.

In the practice of the invention an elongated column is attached to the leg front portion in a relatively parallel relationship. Pads mounted at the upper and lower regions of the column are strapped to the leg wherein the column constitutes a reference element or line with respect to the approximate center line of the leg, and a measurement device selectively movable along the column contains probes for engaging the leg and permitting measurement of the leg relative to the column.

The measurement device comprises a caliper-like apparatus using a pair of spaced probes movable toward and away from each other. The probes are mounted upon a guide having a scale defined thereon whereby the distance of the probe from the column is immediately ascertainable. A plurality of reference indices are defined along the column whereby the measurement apparatus may be selectively raised or lowered to known locations, and the measurement devices utilize a spring biased detent for selectively engaging an index recess defined on the column.

By sliding the probe along the guide for engagement with the side of the leg the transverse location of the engaged portion of the leg relative to the column may be quickly determined by reference to the guide scale, and an operator may take a plurality of leg measurements at various locations along the leg and column in a short time without discomfort or inconvenience to the patient.

BRIEF DESCRIPTION OF THE DRAWINGS

The aforementioned objects and advantages of the invention will be appreciated from the following description and accompanying drawings wherein:

FIG. 1 is a perspective view of leg and knee orthosis measuring apparatus in accord with the invention, FIG. 2 is a front elevational view illustrating the apparatus of the invention as mounted upon the leg of a patient, FIG. 3 is a plan sectional view as taken along a Section III—III of FIG. 1, FIG. 4 is an enlarged, elevational, sectional view as taken through the upper pad along Section IV—IV of FIG. 1, FIG. 5 is an elevational sectional view of the guide and probe inner end as taken along Section V—V of FIG. 3, and FIG. 6 is an elevational view taken through the measurement carriage along Section VI—VI of FIG. 3.

DESCRIPTION OF THE PREFERRED EMBODIMENT

The orthosis measuring device of the invention includes a column 10 such as formed of a cylindrical one half inch diameter rod or tube having an upper end region 12 and a lower end region 14 with the intermediate region 16 being defined therebetween. The upper and lower ends of the column may have caps 17 placed thereon for decorative and protection purposes. A pad indicated at 18 is located upon the column upper end region while a lower pad assembly 20 is mounted upon the column lower end region. The leg measurement means 22 is mounted upon the column intermediate region 16 for selective movement thereon in a vertical direction.

The column mounting pads 18 and 20 are identical except that the upper pad 18 is of a larger dimension in that the pad 18 is associated with the wearer's thigh while the smaller lower pad 20 is mounted to the wearer's ankle. As the structural components of the pads are identical the lower pad components are identified by primed reference numerals.

The pads are attached to the column 10 by blocks 24 and 24' and the blocks each include a vertical bore 26 which slidably receives the column. A set screw and knob assembly 28 and 28' is associated with each of the blocks 24 and 24', respectively, and the set screw assemblies are threaded into threaded holes defined in the associated block intersecting the associated bore 26 for engaging the column and axially and rotatably fixing the associated block to the column.

The pads also each include a synthetic plastic sheet 30 and 30' of a generally rectangular configuration interiorly lined by the foam liner 32 which is bonded to the associated sheet. The sheet and liner assembly is attached to the associated block 24 and 24' by screws 34, FIG. 4.

Straps 36 and 36' are associated with the ends of the pads 18 and 20, respectively, and the straps are mounted to the sheets 30 and 30' and include a buckle 38 and 38' whereby the lengths of the straps can be readily adjusted in the known manner.

The measurement device 22 includes a block-like carriage 40 having a vertical bore 42, FIG. 6, defined therein for slidably receiving the column intermediate region 16. The carriage 40 also includes a transverse bore 44 which intersects bore 42 and a ball 46 is located within bore 44 and is biased to the right, FIG. 6, by spring 48 which engages the threaded plug 50 consisting of an Allen screw for rotation and axial positioning within the bore 44. The spring 48 biases the ball 46 to the right for selective engagement with the recesses 52 defined along the column at axially spaced locations wherein the recesses 52 define indices and the ball 46 constitutes an index for selectively locating the carriage 40 along the column.

An elongated guide 54 is bonded to the top of the carriage 40 having an opening through which the column extends. The guide 54 includes portions extending transversely from both sides of the carriage 40 and the column 10 and indicia 56, FIG. 3, is formed on the guide 54 to indicate the distance from the column 10.

Probes 58 and 58' are slidably mounted upon the lateral portions of the guide 54 and the probes 58 and 58' are identical mirror images of each other. Each of the probes includes an inner leg contact surface 60 or 60', and the inner ends are indicated at 62. A hole 64 is defined in the inner end of each of the probes wherein the indicia 56 formed on the guide 54 may be viewed therethrough, and a reference line 65 is formed on the probe inner ends 62 adjacent the holes 64 so that the position of the probes on the guide 54 may be accurately determined.

The probes are mounted upon the guide 54 by a slide 66, FIG. 5, which includes a U shaped recess 68 closely, but slidably, receiving the guide 54, and screws 70 attach the slide 66 to the probe inner ends 62. In this manner the probes 58 and 58' may be moved in a transverse manner relative to the column 10 and the position of the reference surfaces 60 and 60' from the center of the column 10 can be accurately determined by reference to the indicia 56 to the reference lines 65.

Preferably, to improve visibility and appearance the blocks 24, carriage 40, guide 54, probes 58 and slides 66 are formed of transparent material, such as acrylic.

In use, the apparatus is located at the front part of the patient's leg 72 and the upper pad 18 is located at the upper thigh region and is mounted to the patient's leg by the strap 36 which passes about the lower torso and can be drawn snug by means of buckle 38. In a similar manner the lower pad 20 is located at the ankle 76 and the strap 36' passes around the patient's ankle and is drawn snug by the buckle 38'. The measurement device 22 will normally be located adjacent the patient's knee region 74 as illustrated in FIG. 2.

When the apparatus is mounted upon the patient's leg as shown in FIG. 2 the column 10 will be located in front of the leg and relatively parallel thereto thereby forming a reference line or standard. When installing the device to the leg the column 10 is located in line with leg center line as closely as possible. Once the measurement device is firmly affixed to the leg the technician will locate the carriage 40 upon the column 10 as desired so that the detant ball 46 will be received within a recess 52. The recesses are located upon the column at those locations wherein the most critical measurements are desired, i.e. at the center of the knee, and at predetermined locations above and below the knee centerline, and also at thigh and shin locations. Once the carriage 40 is located upon the column as desired the probes 58 and 58' are moved toward each other until the edges 60 and 60', respectively, engage the side of the leg, and at that time the technician will observe and record the position of each probe to the guide 54 as indicated by reference lines 65 to indicia 56. As the measurement apparatus 22 is moved up and down the leg, and measurements taken at each location, a very accurate record can be made of the patient's leg so that orthosis devices for the knee or leg can be accurately formed, and much of the trial and error fitting process presently utilized with orthosis fittings is eliminated.

The measurement device of the invention is lightweight, inexpensive, is readily usable by technicians of limited skill without discomfort to the patient, and yet, accurate measurements for permitting the fitting of leg and knee orthosis devices is achieved.

It is appreciated that various modifications to the inventive concepts may be apparent to those skilled in the art without departing from the purpose and scope of the invention.

I claim:

1. A knee orthosis measurement device for measuring the dimensional position of portions of a leg and knee relative to a reference line comprising, in combination, a linear reference column having a length, an upper end region, a lower end region and an intermediate region, upper leg orientation means mounted on said upper end region for attaching said upper end region adjacent the leg above the knee, lower leg orientation means mounted on said lower end region for attaching said lower end region adjacent the leg below the knee, and measurement means for measuring portions of the leg relative to said column selectively movable mounted on said intermediate region along the column length, said measurement means including probe means transversely disposed to the length of said column adapted to engage the leg and indicia means for indicating the dimensional spacing of said probe means relative to said column.

2. In a knee orthosis measurement device as in claim 1, said measurement means including a carriage slidably mounted on said column, an elongated guide mounted on said carriage having a length substantially perpendicular to the length of said column, said probe means being movably mounted on said guide for selective movement toward and away from said column said indicia means comprising indicia defined on said guide indicating the dimensional spacing between said column and said probe means.

3. In a knee orthosis measurement device as in claim 2, said carriage including a pair of lateral sides, said elongated guide including a guide portion extending from each carriage lateral side having said indicia defined thereon, wherein said probe means comprises two probes, each of said probes slidably mounted on each of said guide portions whereby a pair of measurements can be simultaneously taken.

4. In a knee orthosis measurement device as in claim 3, said guide portions comprising a linear elongated plate defining a way, and each of said probes including slide means for partially encompassing the guide portion plate upon which the probes are mounted.

5. In a knee orthosis measurement device as in claim 2, a plurality of recesses defined on said column spaced from each other along the column length, and recess engagement means defined on said carriage for selectively engaging said recesses.

6. In a knee orthosis measurement device as in claim 5, said recess engagement means comprising a spring biased detent movably mounted on said carriage.

7. In a knee orthosis measurement device as in claim 1, said upper and lower leg orientation means comprising pads adapted to engage the leg, and a flexible strap associated with each of said pads for attaching the associated pad to the leg.

* * * * *